United States Patent [19]

Oberstar et al.

[11] 4,061,602

[45] Dec. 6, 1977

[54] CONDITIONING SHAMPOO COMPOSITION CONTAINING A CATIONIC DERIVATIVE OF A NATURAL GUM (SUCH AS GUAR) AS THE ACTIVE CONDITIONING INGREDIENT

[75] Inventors: Helen Elizabeth Oberstar, Montville; Morton Alan Westman, Fort Lee, both of N.J.

[73] Assignee: American Cyanamid Company, Stamford, Conn.

[21] Appl. No.: 711,331

[22] Filed: Aug. 3, 1976

[51] Int. Cl.² ............... A61K 7/08; C11D 1/88; C11D 1/94; C11D 3/37
[52] U.S. Cl. ............... 252/547; 252/142; 252/145; 252/153; 252/154; 252/155; 252/173; 252/542; 252/545; 252/546; 252/550; 252/DIG. 2; 252/DIG. 5; 252/DIG. 13; 424/70; 424/78
[58] Field of Search .......... 252/89, 528, 547, 153, 252/154, 155, 173, 142, 144, 145, 524, 542, 550, DIG. 2, DIG. 5, DIG. 7, DIG. 13, 546; 424/70, 71, 78; 536/114

[56] References Cited

U.S. PATENT DOCUMENTS

| 3,580,853 | 5/1971 | Parran | 252/542 |
| 3,589,978 | 6/1971 | Kamal | 162/158 |
| 3,808,311 | 4/1974 | Olson | 424/70 |
| 3,917,817 | 11/1975 | Vanlerberghe | 424/70 |
| 3,958,581 | 5/1976 | Abegg | 424/70 |
| 3,980,769 | 9/1976 | Ohilardi | 424/70 |
| 3,990,991 | 11/1976 | Gerstein | 252/542 |
| 3,992,336 | 11/1976 | Faucher | 424/70 |

FOREIGN PATENT DOCUMENTS 1,136,842  12/1968  United Kingdom ............... 536/114

*Primary Examiner*—Dennis L. Albrecht
*Attorney, Agent, or Firm*—Charles J. Fickey

[57] ABSTRACT

A unitary shampoo-creme rinse composition for improving the combing properties and luster of hair which comprises a single phase aqueous detergent composition containing an amphoteric detergent and an anionic detergent and a cationic derivative of a naturally occurring polymer.

5 Claims, No Drawings

CONDITIONING SHAMPOO COMPOSITION CONTAINING A CATIONIC DERIVATIVE OF A NATURAL GUM (SUCH AS GUAR) AS THE ACTIVE CONDITIONING INGREDIENT

The present invention relates to a unitary shampoo-creme rinse composition for improving the combing properties and luster of hair which comprises a single phase aqueous detergent composition containing an amphoteric detergent and an anionic detergent and a cationic derivative of a naturally occurring polymer.

The possibility of combining shampoo action with creme rinse and conditioning action in a single composition for use in a single treatment of hair had been investigated heretofore. It is known that anionic detergents and polymers are suitable for shampooing and that cationic detergents and polymers are useful as creme rinses. Heretofore the combination of an anionic detergent and a cationic detergent was considered impossible because of inherent incompatibility. It has recently been discovered, however, that anionic detergents are compatible with certain types of cationic polymers and that effective hair conditioning shampoo compositions can be obtained thereby.

We have now discovered that improved combing properties, improved hair conditioning and observable highly desirable shine or luster can be imparted to hair by shampoo compositions which contain proper proportions of an amphoteric and anionic surface active agent and a cationic derivative of a polygalactomannan gum.

The cationic derivatives of polygalactomannan gums which are useful in combination with anionic and amphoteric surface active agents are quaternary ammonium salts as described in U.S. Pat. No. 3,589,978.

Polygalactomannans contain as the basic unit two mannose units with a glycosidic linkage and a galactose unit attached to one of the hydroxyls of the mannose units. On average, each of the sugar units has three available hydroxyl sites. The hydroxyl groups of the polygalactomannan are reacted with certain reactive quaternary ammonium compounds to produce the cationic polymers of the present invention. Various polymers can be obtained thereby depending on the quaternary ammonium compound used and on the degree of substitution (D.S.), up to a mixture of three per sugar unit. The polygalactomannans are available commercially as guar gum or locust bean gum.

The quaternary ammonium compounds which are suitable for preparing the polymers of the invention are defined broadly as conforming to the structure:

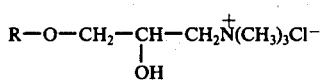

where $R_1$, $R_2$, and $R_3$ are selected from alkyl, substituted alkyl, aryl and substituted aryl groups, $R_4$ is selected from epoxyalkyl and halohydrin groups, and $Z^-$ is an anion such as $Cl^-$, $Br^-$, $I^-$ and $HSO_4^-$.

Epoxyalkyl groups are defined as:

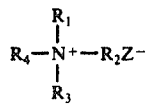

and halohydrin groups as

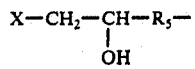

where in each instance $R_5$ is a divalent alkylene radical having 1 to 3 carbon atoms, such as $-CH_2-$, $-CH_2CH_2-$, $-CH_2CH_2CH_2-$ and

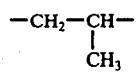

Particularly preferred quaternary ammonium compounds are 2,3-epoxypropyltrimethyl ammonium chloride and 3-chloro-2-hydroxypropyl trimethyl ammonium chloride. Particularly preferred cationic polymers are those represented by the structure:

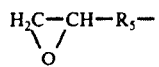

where R represents the polymer molecule.

The shampoo-creme rinse composition of the present invention contains a mixture of one of more amphoteric detergents and one or more anionic detergents, generally in essentially equal amounts, although their relative proportions may vary widely.

Suitable amphoteric detergents include fatty alkyl dicarboxylic derivatives of imidazolines, such as those sold as Miranols; alkyl beta-aminopropionates, such as Deriphats, sold by General Mills; sultaines, such as 1-(myristyl dimethylammonio)-2-hydroxypropane-3-sulfonate, and betaines, such as 1-(myristyl dimethylammonio)acetate, and the like. A preferred amphoteric detergent is the dicarboxylic coconut derivative sold under the name Miranol C2M-SF. The proportion of amphoteric detergent used in the shampoo composition should be sufficient to produce the desired effect of solubilizing the cationic polymer and providing a vehicle for deposition on the hair, but ordinarily will range between 5 and 20 percent by weight, preferably 10 to 17 percent by weight.

Anionic detergents are generally added to the shampoo composition to provide foaming and also to solubilize the polymer. Suitable anionic detergents include sodium lauryl sulfate, sodium polyhydroxy monoether sulfate, cocoyl sarcosine, diethanol/triethanol ammonium lauryl sulfate, triethanolamine lauryl ether sulfate and the like. A preferred anionic detergent is cocoyl sarcosine sold under the trade name Hamposyl C. The anionic detergent is used in an amount ranging from about 5 to 20 percent by weight, preferably 10 to 17 percent by weight.

Suitable nonionic detergents, which provide rinsability and wet and dry conditioning, including polyethylene glycol mono- and distearates, octyl and nonylphenoxy polyethoxyethanol, such as Triton X-100, fatty acid alkanolamides, oxyethylated polypropylene glycols, such as Pluronics (BASF Wyandotte), amine oxides, and the like. A particularly preferred nonionic is polyethylene glycol 6000 distearate, sold by Armak Co. The nonionic detergent may be used in an amount ranging from about 0.1 to 5 percent by weight, preferably 0.1 to 1 percent by weight.

The cationic polymer is used in amount sufficient to impart conditioning action to the hair, but ordinarily is used in an amount of from about 0.1 to 5 percent by weight, preferably 0.2 to 2 percent by weight.

The pH of the composition should be as least about 4.5, to about 8.0, and desirably from about 5.5 to 7.5. The pH may be adjusted to the desired level by the use of an acidic and/or an alkaline material, for example citric acid or water-soluble amines such as triethanolamines. Citric acid also serves as a sequestering agent and a buffering agent and is frequently added for these purposes even if not needed for pH adjustment.

Various other additives are conventionally added to shampoo compositions such as preservatives, dyes, perfumes, antibacterials, and the like.

The following specific example is illustrative of the invention, and will enable persons skilled in the art to better understand and practice the invention.

EXAMPLE

| | % by Weight |
|---|---|
| Dicarboxylic coconut derivative of imadazoline, sodium salt, (Miranol C2M-SF) | 36.00 |
| Mixed diethanol/triethanolammonium laurylsulfate (Standapol 7021) | 5.00 |
| Cocoyl sarcosine (Hamposyl C) | 8.00 |
| Polyethylene glycol distearate, MW 6000 | 0.25 |
| Cationic polymer (1) | 0.48 |
| Preservatives | 0.35 |
| Perfume | 0.30 |
| Citric acid | to pH 5.80 |
| Deionized water | q.s. to 100.00 |

(1) 3-(trimethylamino)-2-hydroxypropyl guar chloride salt; General Mills Chemicals, Inc.

The above formulation was evaluated by professional beauty operators in a professional beauty salon using a test panel of 14 subjects. The operators evaluated the shampoo for both wet and dry hair properties. Using a scale of 1 to 5 (highest) the average wet evaluation was 4.3 and the average dry evaluation was 3.4.

We claim:

1. A shampoo-creme rinse composition consisting essentially of about 5 to 20 weight percent of at least one amphoteric detergent, about 5 to 20 weight percent of at least one anionic detergent and from about 0.1 to 5 weight percent of 3-(trimethylamino)-2-hydroxypropyl guar chloride salt.

2. The composition of claim 1 wherein the pH is about 4.5 to 8.

3. The composition of claim 1 comprising in addition citric acid.

4. The composition of claim 2 wherein an acid or base is added to obtain said pH.

5. The composition of claim 1 comprising in addition from about 0.1 to 5 weight percent of a nonionic detergent.